United States Patent [19]
McShane et al.

[11] Patent Number: 5,827,506
[45] Date of Patent: Oct. 27, 1998

[54] SUNLESS TANNING METHOD AND APPARATUS

[75] Inventors: James E. McShane; Carl Kaplan, both of Memphis; Thomas A. Meyer, Germantown, all of Tenn.

[73] Assignee: Schering-Plough HealthCare Products, Inc., Memphis, Tenn.

[21] Appl. No.: 513,927

[22] PCT Filed: Mar. 30, 1994

[86] PCT No.: PCT/US94/03258

§ 371 Date: Nov. 13, 1995

§ 102(e) Date: Nov. 13, 1995

[87] PCT Pub. No.: WO94/22419

PCT Pub. Date: Oct. 13, 1994

Related U.S. Application Data

[63] Continuation of Ser. No. 40,804, Mar. 31, 1993, abandoned.

[51] Int. Cl.⁶ .............................. A61K 7/42; A61K 7/44; A61K 7/00
[52] U.S. Cl. .............................. 424/59; 424/60; 424/400; 424/401
[58] Field of Search .............................. 424/59, 60, 400, 424/401

[56] References Cited

U.S. PATENT DOCUMENTS

| | | | |
|---|---|---|---|
| 2,176,923 | 10/1939 | Nitardy | 222/94 |
| 3,177,120 | 4/1965 | Black et al. . | |
| 3,290,017 | 12/1966 | Davies et al. . | |
| 3,608,709 | 9/1971 | Pike . | |
| 3,756,389 | 9/1973 | Firth . | |
| 3,809,224 | 5/1974 | Greenwood . | |
| 3,983,994 | 10/1976 | Wyslotsky . | |
| 4,434,154 | 2/1984 | McShane | 424/60 |
| 4,458,811 | 7/1984 | Wilkinson . | |
| 4,496,046 | 1/1985 | Stone et al. . | |
| 4,608,043 | 8/1986 | Larkin | 604/87 |
| 5,137,178 | 8/1992 | Stokes et al. | 222/94 |
| 5,229,104 | 7/1993 | Sottery et al. | 424/59 |
| 5,232,688 | 8/1993 | Ziegler et al. | 424/59 |
| 5,268,166 | 12/1993 | Barnett et al. | 424/47 |
| 5,514,437 | 5/1996 | Tanner et al. | 424/63 |

FOREIGN PATENT DOCUMENTS

| | | | |
|---|---|---|---|
| 0425324 | 5/1991 | European Pat. Off. . | |
| 0547864 | 6/1993 | European Pat. Off. . | |
| 1293290 | 4/1962 | France | 424/63 |
| 54-132243 | 10/1979 | Japan | 424/63 |
| 2062016 | 5/1981 | United Kingdom . | |

OTHER PUBLICATIONS

E. Wittgenstein et al., "Reaction of Dihydroxyacetone (DHA) with Human Skin Callus and Amino Compounds," *Journal of Investigative Dermatology*, vol. 36, pp. 283–286 (1961).

A. Meybeck, "A Spectroscopic Study of the Reaction Products of Dihydroxyacetone with Aminoacids," *Journal of the Society of Cosmetic Chemists*, vol. 28, pp. 25–35 (1977).

*Chemical Abstracts*, vol. 95, Abstract 30226g (1981).

M.F. Bobin et al., "Effects of Color Adjuvants on the Tanning Effect of Dihydroxyacetone," *Journal of the Society of Cosmetic Chemists*, vol. 35, pp. 265–272 (1984).

P. Lister, "Safe Sun," *Self*, May 1992, pp. 135–137 and 177.

D. Debrovner, "Bottled Sunshine," *American Druggist*, Jul. 1992, pp. 42, 47 and 49.

*Primary Examiner*—Shelley A. Dodson
*Attorney, Agent, or Firm*—Eric S. Dicker; John J. Maitner; Robert A. Franks

[57] ABSTRACT

Apparatus for simulating skin tanning comprises a receptacle containing a fluid comprising dihydroxyacetone, a receptacle containing a fluid comprising an amino acid, and dispensing means for simultaneously or sequentially providing desired amounts of dihydroxyacetone and amino acid.

35 Claims, 6 Drawing Sheets

SUNLESS TANNING METHOD AND APPARATUS

The present application is the U.S. national application corresponding to International application No. PCT/US94/03258, filed Mar. 30, 1994 and designating the U.S., which PCT application is in turn a continuation of U.S. application Ser. No. 08/040,804, filed Mar. 31, 1993 now abandoned the benefit of which applications are claimed pursuant to the provisions of 35 U.S.C. 120,363 and 365 (C).

FIELD OF THE INVENTION

This invention relates to apparatus useful in the simulated tanning of skin. More particularly, the invention relates to apparatus used in the treatment of skin with dihydroxyacetone compositions, to form a brownish coloration thereon.

INTRODUCTION TO THE INVENTION

It has long been known that certain compounds form pigments when applied to the skin. Products containing dihydroxyacetone (frequently simply abbreviated "DHA") have been marketed since the early 1960's, and have been found satisfactory by many persons who wish to give their skin the appearance of an attractive tan, but do not desire to risk the now well-appreciated health hazards of exposure to solar or artificially-generated ultraviolet radiation.

However, some persons have not obtained the desired results from DHA applications. A small number of individuals develop a coloration which tends to appear yellowish or orange. Some others, probably due to perspiration, rubbing or washing during the slow generation of color as skin components react with DHA, or to a lack of care to evenly apply the DHA, develop uneven coloration. Many users of the available products would prefer to obtain a more rapid generation of color.

The chemistry of DHA-skin interaction has been investigated by several workers. Wittgenstein and Berry published a paper "Reaction of Dihydroxyacetone (DHA) with Human Skin Callus and Amino Compounds," in *The Journal of Investigative Dermatology*, Vol. 36, pages 283–286 (1961), describing work to characterize the browning phenomenon. They reported that DHA reacts with a number of compounds, including ammonia and amino acids, to form a brown color, and theorized that skin browning is due to the reaction of DHA with free amino groups in the skin, the amino groups probably being on arginine molecules which are present in skin proteins.

A. Meybeck published "A Spectroscopic Study of the Reaction Products of Dihydroxyacetone with Aminoacids" in *Journal of the Society of Cosmetic Chemists*, Vol. 28, pages 25–35 (1977), and characterized brown pigments formed from the reaction of DHA with amino and other acids at 100° C. Further experiments at 37° C. were conducted to better simulate reactions which may occur in the skin: DHA was reacted with the amino acids glycine, lysine, alanine, serine and arginine, but only glycine and lysine produced significant amounts of pigment after 24 hours. It was concluded that DHA must act by initially condensing with free amino acids at the skin surface, followed by polymerization and linking to proteins in the stratum corneum, probably through lysine side chains.

A further study was reported by M. F. Bobin, M. C. Martini and J. Cotte, "Effects of Color Adjuvants on the Tanning Effect of Dihydroxyacetone," *Journal of the Society of Cosmetic Chemists*, Vol. 35, pages 265–272 (1984). This work involved measuring the rate of color development after mixing DHA and various amino acids or their derivatives, and applications of DHA and methionine sulfoxide in vivo. It was concluded that methionine sulfoxide is a useful adjuvant to DHA, as the combination provided rapid color development, plus a more intense and long lasting color than would be obtained with only DHA. This result was thought to result from the affinity of methionine sulfoxide for keratin.

Chemical Abstracts, Vol. 95, abstract 30226g (1981) summarizes a German patent document (3,037,497) pertaining to dyeing skin, hair, feathers, fur, etc. by treating with a mixture of DHA and an amino acid sulfoxide. When DHA and methionine sulfoxide were applied in cream formulations, skin turned a deep brown color after three hours and the color was more resistant to washing than that obtained with only DHA.

Black et al., in U.S. Pat. No. 3,177,120, discussed the problem of including DHA and amino group-containing sunscreens together in a formulation, and concluded that only sunscreens free from amino groups should be used, to prevent formation of a yellow or brown color in the storage container; color formation is also said to be accompanied by inactivation of both the DHA and sunscreen.

Diane Debrovner, in an article entitled "Bottled Sunshine," *American Druggist*, July 1992, describes a recently introduced self-tanning product which is a dual-chamber tube having a DHA-containing cream on one side and a cream containing amino acids on the other. The product is said to create a golden, rather than orange, color on the skin.

An article by Pamela Lister, "Safe Sun," in the magazine *Self*, May 1992, pages 134–137 and 177, describes several sunless tanning products of various manufacturers, including amino acid-containing formulations.

In spite of the teachings in the art relating to the use of DHA with typical formulations of $\alpha$-amino acids and their derivatives, it has been found that color formed thereby does not have a desired substantivity, or resistance to removal by rubbing or washing. Thus, it is desired to provide apparatus and a method for browning skin to form simulated tans having improved substantivity, yet having colors which closely resemble those obtained from exposure to ultraviolet radiation.

SUMMARY OF THE INVENTION

The invention, in one aspect, provides apparatus for imparting artificial tan to skin, comprising: a receptacle containing a fluid formulation comprising dihydroxyacetone; a receptacle containing a fluid formulation comprising an amino acid; and dispensing means for simultaneously or sequentially providing desired amounts of dihydroxyacetone and amino acid. The invention also includes a method for imparting artificial tan to skin, comprising simultaneously or sequentially contacting the skin with dihydroxyacetone and an amino acid. Further included is a composition for prompt application to skin, comprising dihydroxyacetone, at least one amino acid and a suitable carrier.

DETAILED DESCRIPTION OF THE INVENTION

The invention will be described with reference to the accompanying drawings. In the description and claims, all percentages are expressed on a weight basis, unless otherwise noted.

In accordance with the invention, there is provided apparatus for imparting a simulated tan to skin, the apparatus having separate compartments for a formulation containing dihydroxyacetone and a formulation containing an amino acid. As previously noted in the art, it is important to prevent mixing of the active ingredients until a user is ready to make a skin application, to prevent premature reaction and color formation. The apparatus can be configured to simultaneously dispense the formulations, in desired amounts, or to sequentially dispense them. If sequentially dispensed, the formulations can be mixed before spreading onto the skin, or can be spread in the order of dispensing.

Figure 1:
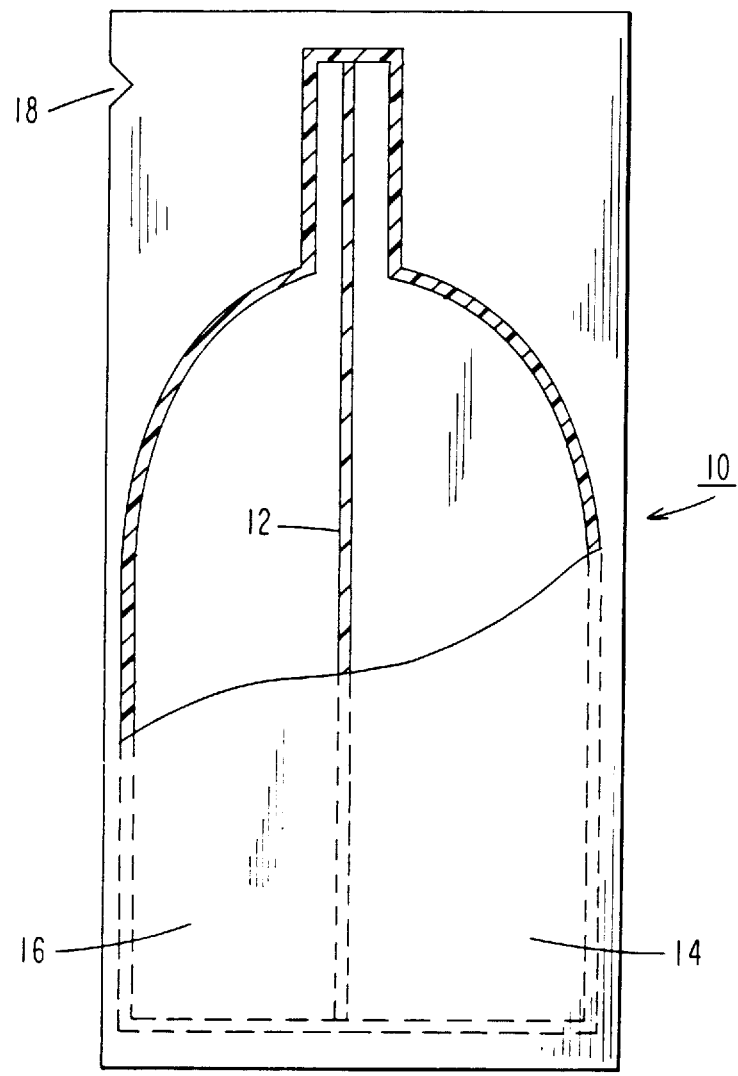
FIG. 1 is a cross-sectional view of a pouch container having two compartments.

Referring to FIG. 1, there are shown the features of a two-compartment pouch 10. Included is septum 12 which, in the least complex embodiment where the pouch comprises heat sealed layers of a thermoplastic substance, is merely a heat sealed seam to divide the volume of the pouch. This septum divides the volume into chambers 14 and 16. Tearing notch 18 can be provided to facilitate removal of the top of the pouch, when it is desired to dispense formulations contained therein. This embodiment will be used primarily for single-use quantities, the pouch holding an appropriate quantity for application once to the whole body or a portion thereof, such as only the face.

As an alternative to a tearing notch, the user can simply cut off the top of the pouch with scissors or a knife. Further, rather than dispensing the two formulations from the pouch in two streams, as would be done with the configuration depicted, septum 12 can be made frangible; applying pressure with the fingers to one side of the pouch will rupture the septum and permit mixing of the formulations by sequentially applying pressure to the two sides, after which a single composition containing both DHA and amino acid can be applied. Of course, such mixing should only be conducted promptly before use.

For sequential application of the two formulations, another tearing notch (not shown) can be provided on the opposite side of the pouch from notch 18, and the septum can be extended to the uppermost limit of the pouch. This will permit only one compartment to be opened by pulling above a notch.

Figure 2:
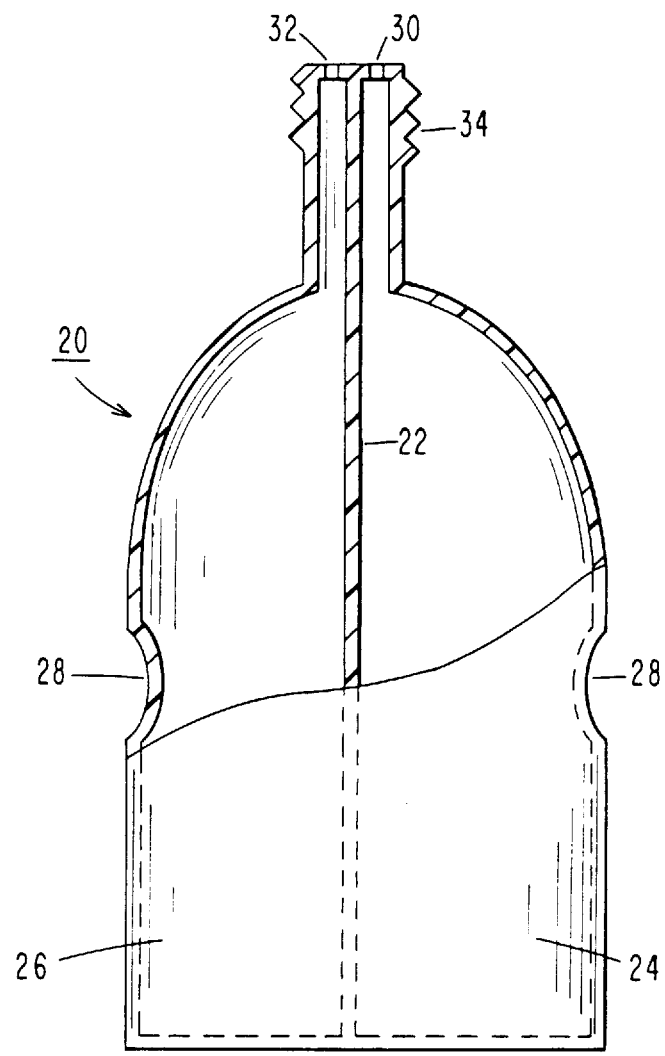
FIG. 2 is a cross-sectional view of a squeeze bottle having two compartments.

FIG. 2 is a view of a squeeze bottle 20, which is provided with septum 22 to form two compartments 24 and 26. The bottle is conveniently formed by molding with thermoplastic substances, as is well known in the art. In a typical embodiment, threads 34 will be provided for closure with a conventional screw cap (not shown). The threads will not be needed if the bottle is closed by alternative means, such as a pressed on flip cap.

Preferably, gripping indentations 28 are provided, to ensure that the bottle is squeezed in locations which will apply approximately uniform pressure to the two compartments, i.e., not to a less deformable area such as that directly over the septum. Upon pressure application, formulations are dispensed from the compartments through orifices 30 and 32.

The bottle can be used for sequential applications of DHA and amino acid, by providing separate closures for the two orifices. As an example, individual snap caps can be provided over the orifices. The user would be required to dispense an appropriate amount of a component, rub that component into the skin and, promptly or after a prescribed time, apply the second component to the skin in a similar manner. Application of equal amounts of the components can be accomplished with sufficient accuracy by noting the lengths of dispensed fluids on the skin; the bottle can be provided with length scales marked thereon to make this more convenient.

Figure 3:
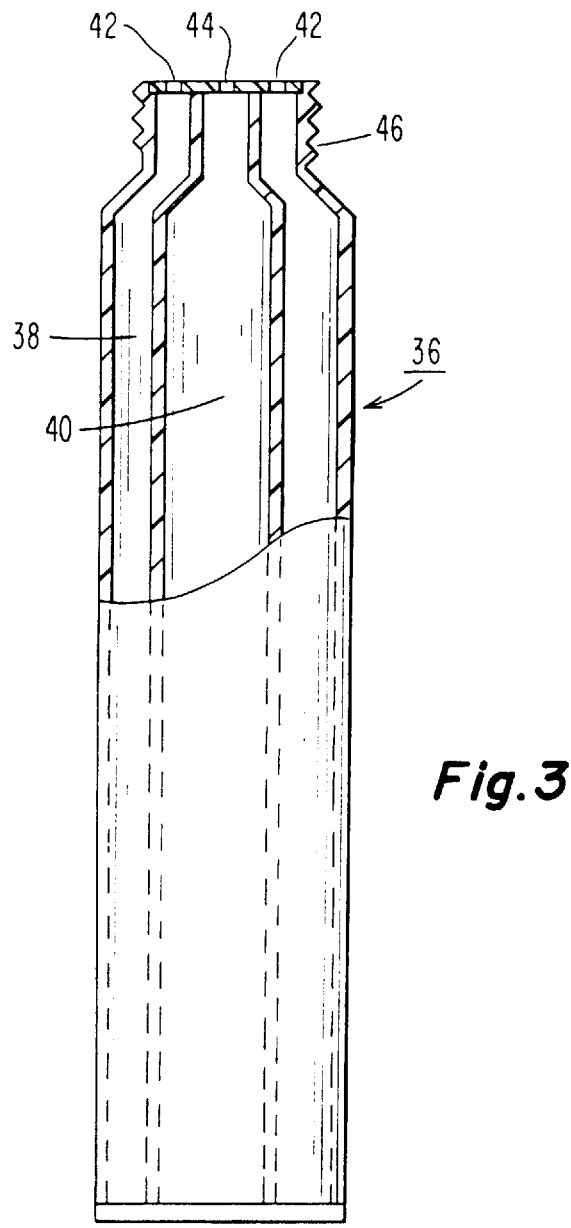
FIG. 3 is a cross-sectional view of a dual-compartment tube container.

Referring now to FIG. 3, there is shown a cross-sectional view of a collapsible tube assembly 36 which is useful in the invention. As shown, the outer tube 38 surrounds the inner tube 40, and contents of the outer and inner tubes can be discharged through outlets 42 and 44, respectively, by squeezing the assembly. A threaded area 46 is provided for attachment of a closure (not shown). Any desired number of outlets can be provided for the tubes and any desired type of closure can be used, the invention not being restricted to a threaded cap.

The assembly can be fabricated from any materials normally utilized for tubes dispensing medications, cosmetic materials, hygiene products such as toothpastes, cleaning compositions and the like, subject to the usual requirement that the materials of construction do not react with formulations contained therein to an appreciable extent during at least the expected storage term. Frequently used materials include metals, polymers and composites, including laminates. Typically, the assembly will be closed at its bottom end by crimping or heat sealing, depending upon the materials of construction. To assure that formulations are dispensed in predetermined relative amounts from the outer and inner tubes, means (not shown) such as a key can be provided at the bottom of the assembly for uniformly collapsing the tubes; as the bottom of the assembly is wound around a rotated key, approximately the same pressure will be applied to the two tubes.

Figure 4:
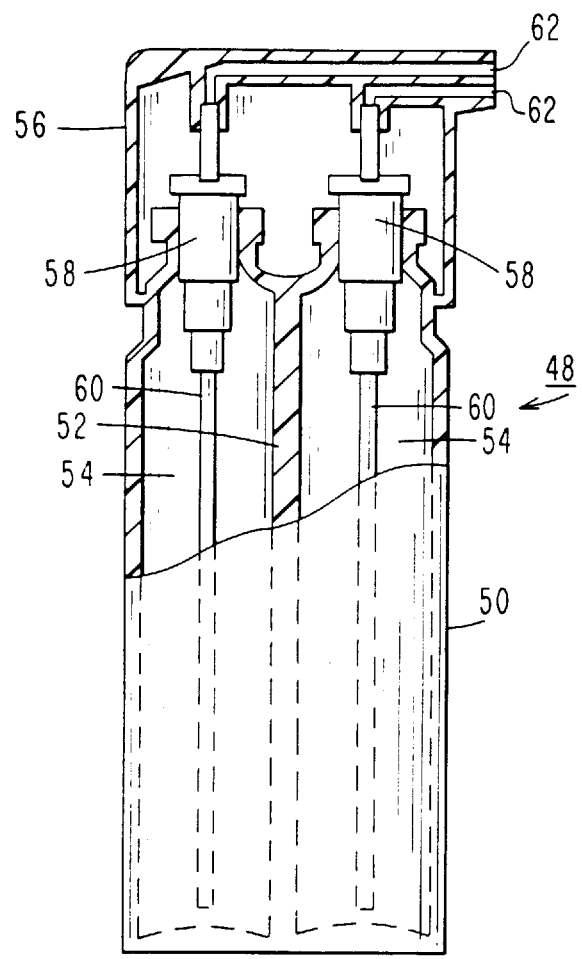
FIG. 4 is a cross-sectional view of a container having two compartments and a dual pump dispenser.

A further apparatus is shown in cross-section as FIG. 4. In this figure, dispensing container 48 comprises bottle 50, having dividing septum 52 which forms two compartments 54 having any desired geometry. Cap 56 is adapted to fit over the outlets of pumps 58, mounted to close the compartments and which can be any of the well-known spring loaded check valve pumps such as are used with hand lotions and other cosmetic products. Pressing down on the cap causes formulations to be simultaneously dispensed from conduits 62; releasing the cap permits it to rise under pressure from springs in the pumps, simultaneously reloading the pumps with stored formulations through dip tubes 60.

This apparatus requires no particular care on the part of the user to obtain a correct ratio of the formulations, in cases where the formulations are to be simultaneously dispensed and applied, but permits complete separation of the components until dispensing. By providing separate caps over the pumps, it would be possible to dispense the formulations at different times, should this be desired. In either embodiment, reproducible amounts will be dispensed simply by pressing the cap down for its full length of travel each time, without any need for a user to make measurements.

Figure 5:
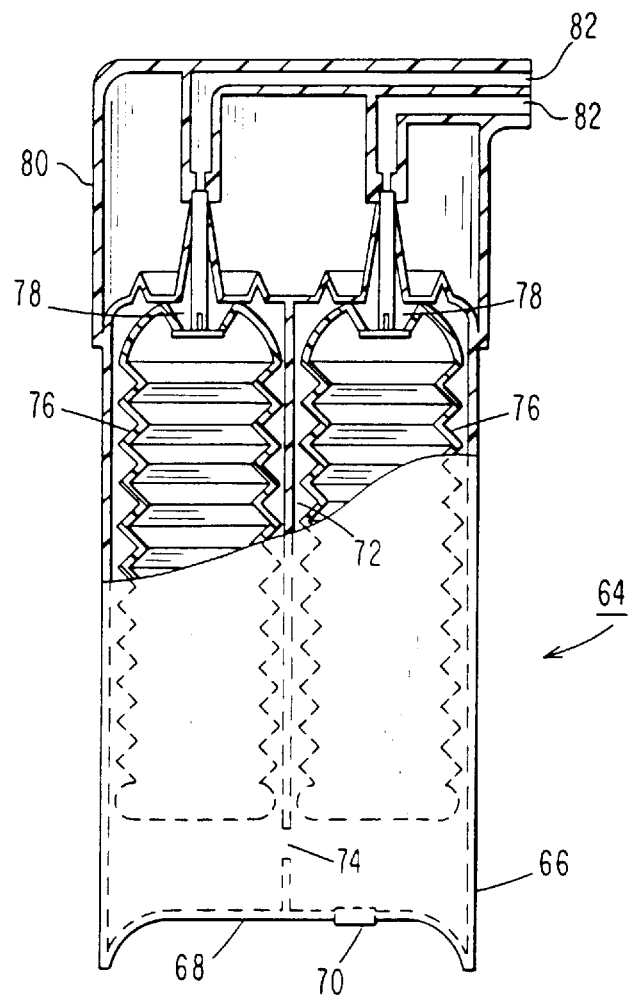
FIG. 5 is a cross-sectional view of a dual-compartment pressurized dispensing container.

FIG. 5 relates to a pressurized aerosol container which can be used to dispense two components simultaneously. Container 64 comprises external shell 66, with bottom closure 68 attached; preferably, both of these components will be fabricated from metals, with the bottom closure crimped or welded to the shell. Gas filling port 70 is provided to seal the container after a pressurizing gas is introduced.

The container is divided by barrier 72, which is provided with one or more perforations 74 near the bottom of the container, to equalize gas pressure in the two sections formed by the barrier. Each section has an accordion-pleated bag 76, preferably fabricated from a plastic material, to contain a formulation, the bags each being connected to an aerosol valve 78 which is actuated to release formulation by its depression into the container. Cap 80 is utilized to simultaneously depress the valves, and directs formulations through conduits 82 for application to a desired area.

This apparatus has the advantages of dispensing desired relative amounts of the contained formulations without any special care on the part of the user, and being very simple to use. By using plastic bags to contain the formulations, the aerosol container needs not be chemically compatible with the formulations, and the propellant will not normally be in contact with the formulations. Of course, costs can be reduced by changing the design to make use of sealed compartments having pistons driven by gas pressure to force formulations out through the valves, but piston sealing, compatibility of construction materials with the formulations and other considerations will complicate the product design. Many alternatives will be apparent to those skilled in aerosol container packaging.

Another useful package for the present invention has two compartments, divided by a removable or frangible barrier. An example is the collapsible tube of U.S. Pat. No. 2,176,923 to Nitardy, where two substances are separated in a tube by a transverse partition which is a collapsible disk having a central aperture; expressible plugs in the aperture are removed by applying pressure to the bottom of the tube, causing the substances to mix. U.S. Pat. No. 3,290,017 to Davies et al. is related, having a disc which can be moved from a barrier position to a mixing position in a tube by external finger pressure.

A further example is found in U.S. Pat. No. 3,608,709 to Pike, where a multiple-compartment laminated pouch is described. This pouch, when external pressure is applied, will form a single compartment by breakage of the internal barrier, permitting two formulations contained therein to mix. Other packages having frangible internal barriers are shown in the following U.S. Pat. Nos.: 3,756,389; 4,458,811; and 4,608,043; these can be adapted for use in the present invention.

U.S. Pat. No. 3,809,224 to Greenwood shows another useful package, having an external clamp divider seal which can be removed to permit mixing of components stored separately when the clamp is in place.

Each of these packages having a frangible or removable barrier will be suitable for single use unit packaging only, since it will be necessary to use the entire contents of the package promptly after the DHA and amino acid formulations are mixed, due to the previously discussed reaction.

Alternatively, the DHA formulation (e.g., in the form of a lotion) can be provided together with a small container (e.g., a vial or pouch) of the amino acid. The consumer will, upon opening the package, combine the amino acid with the DHA formulation and thus prepare a mixture for repeated applications, which will be stable during short periods of storage—typically not more than about one month when using the DHA lotion formulation of following Example 3, the actual storage life depending upon storage conditions. Preferably, the DHA formulation container will be substantially clear or be provided with a clear window, so that color formation can be easily detected. The user will be instructed to apply the mixed product promptly, i.e., before significant color generation in the container, then discard all remaining portions.

The foregoing is a description of representative packaging techniques for maintaining and dispensing a formulation comprising dihydroxyacetone and a formulation comprising an amino acid. Both formulations must be fluid, that is, capable of flow under the influence of gravity or a moderate externally applied pressure. Examples of useful fluid formulations are ointments, dispersions such as creams and lotions, gels, solutions, and the like, each of which (and preparative techniques therefor) are very well known to those skilled in the formulating art.

Typically, both formulations which are to be used together will be of the same type, e.g., if one is a gel, the other also will be a gel to facilitate application and mixing. However, it is not always necessary to observe this general principle.

Amino acids which are useful in preparing the formulations of the invention have the general formula $RCH(NH_2)COOH$, where R is hydrogen or a substituted or unsubstituted hydrocarbyl group, permissible substituents being halogens, nitrogen-containing groups, sulfur-containing groups, hydroxy groups, carbonyl-containing groups, and the like. In general, the amount of heteroatom substitution in a hydrocarbyl group will be less than one such atom per each five carbon atoms in the group and, usually, there will be no heteroatoms, i.e., the group will be hydrocarbon. It should be noted that more than one amino group can be present in a compound; primary amino groups are not considered to be "heteroatom-containing" for purposes of this invention. Useful amino acids include, without limitation, glycine, alanine, valine, leucine, phenylalanine, serine, lysine, arginine, threonine, methionine and others, alone or in combination. Glycine is a presently preferred amino acid.

Volumes and active ingredient concentrations of dispensed formulations should be chosen to provide molar ratios of DHA to primary amino groups about 0.5 to about 14. It is generally useful to provide formulations which, when mixed, contain about 0.04 to about 0.12 molar concentrations of primary amino groups, preferably about 0.06 to about 0.1 molar and more preferably about 0.075 to about 0.085 molar. When the amino acid is glycine, the formulations generally will be used in proportions and concentrations which produce a mixture having about 0.25 to about 0.9 percent glycine, with about 0.45 to about 0.75 percent being preferred and about 0.55 to about 0.65 percent being more preferred.

If the number of moles of DHA exceed the number of moles of primary amino groups, a portion of the DHA will remain free to react with amino groups in the skin, increasing the substantivity of the color formed; thus, a molar excess of DHA is preferred. Although the rate of color formation in the skin (with free amino groups present there) is considerably slower than that of DHA with provided amino acid on or near the skin surface, color formed in the skin is much more resistant to removal by washing and abrasion. For this reason, it is preferable to establish both the early and frequently more intense color on the skin surface, and the more permanent but slower forming color in the skin layers.

It has been found that pH at the time of application affects the resulting color. In general, either the DHA formulation or the amino acid formulation should be able to establish pH values about 3 to about 13 locally when applied to the skin. More preferred are values about 7 to about 11, with values about 8 to about 10 being particularly preferred with some formulations. The optimal pH for a given amino acid application will be somewhat dependent upon the $pK_a$ of that amino acid, and can be easily determined by applying formulations having different pH values to the skin.

To compare simulated tans created by different means, it is helpful to have an objective, instrumental measurement of colors and intensities. Accordingly, a method has been developed using a Minolta Chroma Meter CR-200, which analyzes reflected light from a surface and gives results in terms of the CIE (International Commission on Illumination) tristimulus values. These values are subsequently transformed mathematically into the L* a* b* color space, wherein the magnitudes of changes in hue and intensity of color correspond closely with those percieved by the human eye.

L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y axis, to give quantitative color information: "metric chroma" is the length of a line from the origin (a*=0, b*=0) to the point of a sample reading, while "metric hue angle" is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The meter is used to measure natural tans with a number of subjects, to establish a target for the appearance of tans produced by DHA reactions. In general, it is found that points on a chromaticity plot for dark tans will have b* from about 19 to about 24, with a* ranging from about 10 to about 14. For medium tans, b* will be about 20 to about 24, with a* from about 9 to about 12. For light tans, b* will be about 18 to about 20, with a* about 7 to about 10. Rather than being a point, the target color is represented by the area on the plot where natural tans lie. Values of metric chroma increase steadily as tans progress from light to medium, but increase much more slowly as tans become more dark than "medium." In contrast, values of metric hue angle overlap significantly for light, medium and dark tans, except for very dark tans which have increased redness (decreased metric hue angle).

Metric lightness is the third required parameter for characterizing natural tans. L* values decrease as tans become darker, a difference of about one unit being discernable to a trained observer. For natural tans, L* ranges from about 47 to about 53 for dark tans, about 54 to about 57 for medium tans and about 58 to about 64 for light tans.

The meter is also used to measure the characteristics of simulated tans obtained using only DHA applications. Several subjects are treated with an oil in water emulsion containing 5 percent DHA, with applications (2 mg DHA/$cm^2$) being made once each day for four days. After the first day, values for b* are about 13 to about 21, the a* values are about 3 to about 8 and L* values are about 63 to about 74. After two days, b* is about 15 to about 23, a* is about 5 to about 8 and L* is about 62 to about 72. After the third day, b* is about 16 to about 23, a* is about 5 to about 9 and L* is about 61 to about 71. After four days, b* is about 17 to about 24, a* is about 5 to about 9 and L* is about 61 to about 70. The hues for all but a few of the readings are more yellowish than the tan target area, and all but a few of the readings indicate tans more light than natural tans, even though comparable levels of metric chroma are generated. It can generally be stated that simulated tans using only DHA are more yellow and lighter than natural tans having similar extents of color formation.

The following examples are provided to illustrate various aspects of the invention, and are not to be construed as limiting the invention in any manner.

EXAMPLE 1

A lotion containing 1.1 percent glycine is prepared from the following ingredients:

| Component | Grams |
| --- | --- |
| Part A | |
| Water | 77.00 |
| Glycine | 1.10 |
| Sodium chloride | 0.50 |
| Glycerin | 2.50 |
| Part B | |
| Water | 0.099 |
| Coloring agent | 0.001 |
| Part C | 1.00 |
| Preservative | |
| Part D | |
| Emulsifier | 3.00 |
| Emulsifying wax | 1.00 |
| Cyclomethicone | 4.00 |
| Isododecane | 8.40 |
| Benzyl alcohol | 1.00 |
| Jojoba oil | 0.10 |
| Aloe Vera lipoquinone | 0.10 |
| Vitamin E acetate | 0.10 |
| Dimethicone | 0.10 |

The lotion is prepared by: adding each of the Part A ingredients to the water in listed order, and heating to about 70° C. with constant mixing; dissolving the coloring agent to the water of Part B, mixing and adding to the Part A solution; adding the preservative with mixing and maintaining the elevated temperature; combining all of the Part D ingredients and heating to about 70° C. with mixing; and slowly adding the heated aqueous mixture to the heated Part D minture, with rapid mixing, to form smooth emulsion. Mixing is continued until the emulsion has cooled.

EXAMPLE 2

A lotion containing 0.88 percent glycine is prepared using the following ingredients:

| Component | Grams |
| --- | --- |
| Part A | |
| Water | 76.9685 |
| Glycerin | 2.50 |
| Glycine | 0.88 |
| Sodium chloride | 0.50 |
| Preservative | 1.00 |
| Coloring agents | 0.10015 |

-continued

| Component | Grams |
|---|---|
| Benzyl alcohol | 1.00 |
| Part B | |
| Cyclomethicone | 4.00 |
| Isododecane | 8.40 |
| Jojoba oil | 0.10 |
| Aloe Vera lipoquinone | 0.10 |
| Vitamin E acetate | 0.10 |
| Dimethicone | 0.10 |
| Fragrance | 0.25 |
| Emulsifying wax | 1.00 |
| Emulsifier | 3.00 |

The formulation is prepared by: adding the Part A ingredients to the water and mixing until dissolved; adding the Part B ingredients to the aqueous solution, in the listed order, with gentle mixing; mixing vigorously for about ten minutes; then separately metering the oil and aqueous phases into a high shear mixer and recirculating into the original mixing vessel, to produce an emulsion having the desired viscosity.

EXAMPLE 3

A lotion containing 7.5 percent DHA is prepared from the following ingredients:

| Component | Grams |
|---|---|
| Part A | |
| Water | 73.20 |
| Sodium chloride | 0.50 |
| Dihydroxyacetone | 7.50 |
| Preservative | 1.00 |
| Part B | |
| Emulsifier | 3.00 |
| Emulsifying wax | 1.00 |
| Cyclomethicone | 4.00 |
| Isododecane | 9.40 |
| Jojoba oil | 0.10 |
| Aloe extract | 0.10 |
| Vitamin E acetate | 0.10 |
| Dimethicone | 0.10 |

The lotion is prepared by heating the water to about 70° C. and adding remaining Part A components to form a solution, forming a solution of the Part B components at about 70° C., and very slowly adding the heated Part A solution to the heated Part B solution, with vigorous stirring.

EXAMPLE 4

Substantivity to water rinsing indicates the water solubility of the color formed, water solubility being an indication of potential problems of streaking and clothing staining from perspiration, exposure to rain, etc. A suitable test involves measuring skin color with the Minolta Chroma Meter, applying formulations to the skin, allowing color to develop, then repeating the color measurement. A gentle stream of luke-warm tap water is allowed to flow over the treated skin for two minutes, then the skin is dried with paper towels. A final skin color measurement is then taken, thirty minutes later. Values of $\Delta E$ can be calculated from the following formula:

$$[(L^*_U-L^*_T)^2+(a^*_U-a^*_T)^2+(b^*_U-b^*_T)^2]^{1/2}$$

where the subscripts "U" represent readings with untreated skin and the subscripts "T" represent readings with treated skin. Thus, $\Delta E$ always represents total color difference between treated and untreated skin.

Substantivity to rubbing is determined by the measurements of color both before and after a 10×8 centimeter, 500-gram block, fitted with a towel covering its lower surface, is pulled across the skin through five cycles, using a back-and-forth motion. This test is conducted first with the towel dry, giving "Dry" results in the following table, and then with the towel saturated with water, giving "Wet" results.

For this example, DHA and glycine formulations are applied to skin immediately after initial readings are taken with the Minolta Chroma Meter, using 25 µl each of a DHA formulation and a glycine formulation, rubbed into a 25 cm² skin area. A period of five hours is allowed for color development, then readings are again taken; the difference in total color is termed "$\Delta E$ Initial" for the tables which follow. After each of water rinsing, dry rubbing and wet rubbing, measurements are made and $\Delta E$ is again determined.

In the experiment, the "invention" product is considered to be the DHA and glycine lotion formulations of preceding Examples 1 and 3. The "commercial" product consists of DHA and glycine lotion formulations contained in a dual-compartment dispenser of the commercially available "Spa for the Sun, The Natural Look, Self Tanner for the Face, SPF 15" by Elizabeth Arden Co., New York, N.Y. U.S.A., which lists the ingredients on its label as follows:

FIRST COMPONENT

Active Ingredients:

Ethylhexyl p-methoxycinnamate
Oxybenzone
Other Ingredients:

Water
Cyclomethicone
Propylene glycol
Glycine
$C_{12-15}$ alkyl benzoate
Aloe Vera gel
Cetyl dimethicone
Polyglyceryl ricinoleate
Trihydroxystearin
Lysine hydrochloride
Ornithine hydrochloride
Sodium hyaluronate
Chamomile extract
Mallow extract
Rosemary extract
Sambucus extract
Tocopheryl linoleate
Cetyl dimethicone copolyol
Methicone
Sodium chloride
Methylparaben
Propylparaben
Fragrance
Sodium dehydroacetate
DMDM hydantoin
Trisodium EDTA
Titanium dioxide
SECOND COMPONENT Active Ingredients:

Ethylhexyl p-methoxycinnamate
Oxybenzene
Other Ingredients:

Water
Dihydroxyacetone
Cyclomethicone

-continued

C$_{12-15}$ alkyl benzoate
Cetyl dimethicone
Polyglyceryl ricinoleate
Trihydroxystearin
Cetyl dimethicone copolyol
Methicone
Propylene glycol
Sodium chloride
Methylparaben
Propylparaben
DMDM hydantoin
Trisodium EDTA
Iron oxides
Titanium dioxide The Elizabeth Arden product has been found by analysis to contain about 3.72 percent glycine, about 0.1 percent lysine compounds and about 0.09 percent ornithine compounds in the first component, and about 7.3 percent DHA in the second component. Its dispenser delivers approximately equal amounts of the two lotions, upon actuation.

|  | ΔE | | | |
|---|---|---|---|---|
| Product | Initial | Rinse | Dry | Wet |
| Invention | 4.0 | 3.4 | 4.2 | 3.1 |
| Commercial | 5.8 | 3.8 | 6.0 | 3.5 |

In the following restatement of the results, "% Color Remaining" is calculated by the equation ($\Delta E_{AFTER}/\Delta E_{INITIAL} \times 100$), where "after" values result from measurements following a particular procedure and "initial" values result from measurements taken prior to that procedure. Data in this table more clearly show that, although the commercial product initially gives a more intense color than the product of the invention (as shown in the preceding table), that coloration is considerably more water-soluble than is the coloration from the inventive product.

| | % Color Remaining | | |
|---|---|---|---|
| Product | Rinse | Dry | Wet |
| Invention | 84 | 109 | 77 |
| Commercial | 66 | 108 | 62 |

EXAMPLE 5

Skin on 25 cm² areas of the inner forearms of eight subjects is treated with 0, 12.5, 25 or 50 μl of a glycine formulation as in Example 1 (except containing 0.10015 grams of a mixture of coloring agents and 0.25 grams of fragrance, and having 0.3505 grams of water deleted from the formulation), 25 μl of a DHA formulation as in Example 3 (except that the fragrance is replaced by an equivalent weight of water), and sufficient quantities of a similar placebo lotion (containing neither glycine nor DHA) to total 75 μl on the skin sites. Additionally, two other 25 cm² skin sites are treated with either 0 or 50 μl of the glycine formulation, 50 μl of the DHA formulation and sufficient placebo lotion to total 100 μl. Skin color is measured with the Minolta Chroma Meter before any formulations are applied.

Five hours after application, the skin sites are measured for color with the Minolta Chroma Meter, rinsed with warm running tap water for about two minutes, dried with paper towels, allowed to air dry for 15 to 20 minutes, and are again measured with the meter. Values of ΔE are calculated as in the preceding example and are shown in the following table. The glycine amounts shown in the table are expressed in μmoles per 25 cm² of skin area.

| | Moles DHA per | ΔE | |
|---|---|---|---|
| Glycine | Mole Glycine | Before Rinsing | After Rinsing |
| Application Density = 3 μl/cm² | | | |
| 0 | — | 3.25 | 3.19 |
| 1.83 | 11.4 | 4.02 | 3.93 |
| 3.66 | 5.7 | 4.35 | 4.01 |
| 7.33 | 2.8 | 4.59 | 3.41 |
| Application Density = 4 μl/cm² | | | |
| 0 | — | 3.98 | 3.64 |
| 7.33 | 5.7 | 5.31 | 4.04 |

These results are restated in the table below after subtracting the mean ΔE value for the DHA-induced color (without glycine) from the preceding values, and calculating the percentage increase in ΔE attributable solely to the glycine content (before rinsing) and the percent of formed color due to the glycine content which remains after rinsing.

| Glycine | Moles DHA per Mole Glycine | Color Increase | Color Remaining |
|---|---|---|---|
| Application Density = 3 μl/cm² | | | |
| 1.83 | 11.4 | 24 | 96 |
| 3.66 | 5.7 | 34 | 75 |
| 7.33 | 2.8 | 41 | 16 |
| Application Density = 4 μl/cm² | | | |
| 7.33 | 5.7 | 33 | 30 |

Figure 6:
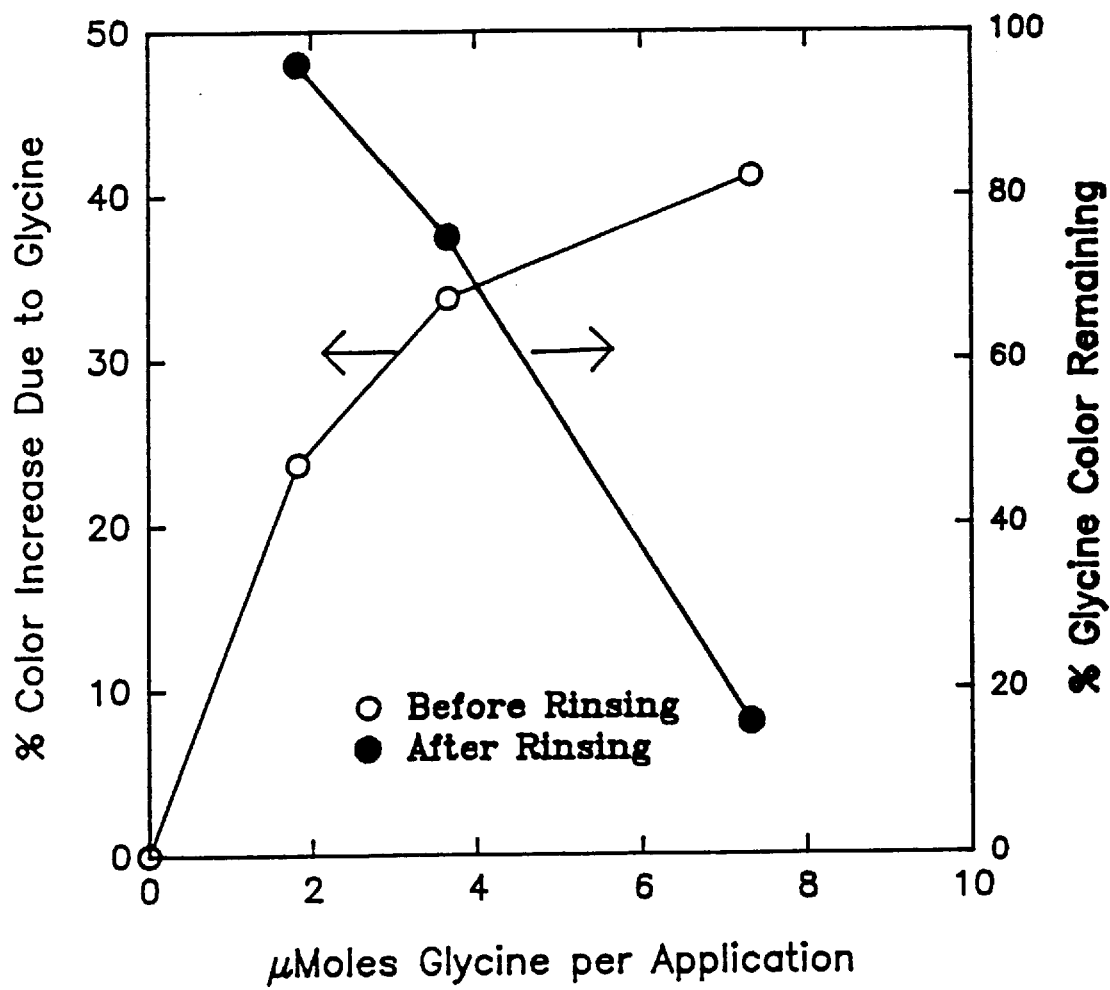
FIG. 6 is a graphical representation of results from an experiment described in Example 5.

The results from this second table are represented graphically in FIG. 6. From the numerical results it can be clearly seen that, although more color is formed by higher amino acid levels applied with a given molar excess of DHA, such color is primarily water-soluble. A balance must be taken between the total initial amount of color and the relative permanence of the color; the optimal amount of glycine occurs where the two lines cross on the graph. Color formed by the reaction of glycine and DHA will decrease the eventual coloring formed by reaction of the DHA with skin, since less DHA will be available for the slower (but more permanent) skin reaction.

By conducting this simple experiment, optimal concentrations for other amino acids and desired levels of DHA can be determined.

The invention has been described with respect to several specific embodiments, but is not to be limited to those embodiments, the scope of the invention being defined only by the appended claims. Various improvements, alternatives and equivalents will be apparent to those skilled in the art upon reading the foregoing description and examples, and such are included within the claimed invention.

What is claimed is:

1. Apparatus for imparting artificial tan to skin, comprising:
   (a) a receptacle containing a fluid formulation comprising dihydroxyacetone;
   (b) a receptacle containing a fluid formulation comprising an amino acid; and (c) dispensing means for simultaneously or sequentially providing amounts of dihydroxyacetone and amino acid which will establish a primary amino group concentration about 0.04 to 0.12 molar in a mixture of the formulations.

2. The apparatus of claim 1, wherein at least one of dihydroxyacetone and amino acid is present in a solution.

3. The apparatus of claim 1, wherein at least one of dihydroxyacetone and amino acid is present in an emulsion.

4. The apparatus of claim 1, wherein at least one of dihydroxyacetone and amino acid is present in a gel.

5. The apparatus of claim 1, wherein the dispensing means provides about 0.06 to about 0.1 molar primary amino group in the mixture.

6. The apparatus of claim 5, wherein the dispensing means provides about 0.075 to about 0.085 molar primary amino group in the mixture.

7. The apparatus of claim 1, wherein the molar ratio of dihydroxyacetone to primary amino group is at least about 1.

8. The apparatus of claim 1 wherein at least one formulation establishes pH values about 3 to about 13, when desired amounts of the formulations are mixed.

9. The apparatus of claim 8, wherein pH values about 7 to about 11 are established.

10. The apparatus of claim 8, wherein pH values about 8 to about 10 are established.

11. The apparatus of claim 1, wherein the amino acid has the formula $RCH(NH_2)COOH$, in which R is hydrogen or a hydrocarbyl group.

12. The apparatus of claim 1, wherein the amino acid is glycine.

13. The apparatus of claim 12, wherein the dispensing means provides about 0.3 to about 0.9 percent glycine in the mixture.

14. The apparatus of claim 12, wherein the dispensing means provides about 0.45 to about 0.75 percent glycine in the mixture.

15. The apparatus of claim 12, wherein the dispensing means provides about 0.55 to about 0.65 percent glycine in the mixture.

16. A method for imparting artificial tan to human skin, comprising contacting the skin with a formulation containing dihydroxyacetone and a formulation containing an amino acid having the formula $RCH(NH_2)COOH$, wherein R is hydrogen or a hydrocarbyl group, the formulations when mixed containing about 0.04 to about 0.12 molar primary amino group.

17. The method of claim 16, wherein the dihydroxyacetone and amino acid are applied to skin sequentially.

18. The method of claim 16, wherein the dihydroxyacetone and amino acid are applied to skin substantially simultaneously.

19. The method of claim 16, wherein a formulation containing dihydroxyacetone and amino acid is applied to skin.

20. The method of claim 16, wherein pH values between about 3 and about 13 are established as skin is initially contacted.

21. The method of claim 20, wherein pH values between about 7 and about 11 are established.

22. The method of claim 20, wherein pH values between about 8 and about 10 are established.

23. The method of claim 16, wherein the concentration of primary amino group is about 0.06 to about 0.1 molar in the mixture of formulations.

24. The method of claim 16, wherein the concentration of primary amino group is about 0.075 to about 0.085 molar in the mixture of formulations.

25. The method of claim 16, wherein the amino acid is glycine.

26. The method of claim 25, wherein the concentration of glycine is about 0.3 to about 0.9 percent in the mixture of formulations.

27. The method of claim 25, wherein the concentration of glycine is about 0.45 to about 0.75 percent in the mixture of formulations.

28. The method of claim 25, wherein the concentration of glycine is about 0.55 to about 0.65 percent in the mixture of formulations.

29. A composition for prompt application to skin, comprising a mixture of:
 (a) a formulation containing dihydroxyacetone; and
 (b) a formulation containing an amino acid having the formula $RCH(NH_2)COOH$, wherein R is hydrogen or a hydrocarbyl group;

the composition having a primary amino group concentration about 0.04 to about 0.12 molar.

30. The composition of claim 29, wherein the concentration of primary amino group is about 0.06 to about 0.1 molar.

31. The composition of claim 29, wherein the concentration of primary amino group is about 0.075 to about 0.085 molar.

32. The composition of claim 29, wherein the amino acid is glycine.

33. The composition of claim 32, wherein the concentration of glycine is about 0.3 to about 0.9 percent.

34. The composition of claim 32, wherein the concentration of glycine is about 0.45 to about 0.75 percent.

35. The composition of claim 32, wherein the concentration of glycine is about 0.55 to about 0.65 percent.

* * * * *